(12) United States Patent
Cavato et al.

(10) Patent No.: US 7,705,216 B2
(45) Date of Patent: Apr. 27, 2010

(54) CORN EVENT PV-ZMIR13 (MON863) PLANTS AND COMPOSITIONS AND METHODS FOR DETECTION THEREOF

(75) Inventors: Tracey A. Cavato, St. Charles, MO (US); Timothy R. Coombe, Ellisville, MO (US); Scott C. Johnson, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 204 days.

(21) Appl. No.: 10/523,290

(22) PCT Filed: Jul. 23, 2003

(86) PCT No.: PCT/US03/22860
§ 371 (c)(1),
(2), (4) Date: Oct. 19, 2005

(87) PCT Pub. No.: WO2004/011601
PCT Pub. Date: Feb. 5, 2004

(65) Prior Publication Data
US 2006/0095986 A1 May 4, 2006

Related U.S. Application Data

(60) Provisional application No. 60/399,279, filed on Jul. 29, 2002.

(51) Int. Cl.
*A01H 5/00* (2006.01)
*A01H 5/10* (2006.01)
*C12N 15/82* (2006.01)

(52) U.S. Cl. .................................. 800/320.1; 424/750

(58) Field of Classification Search ....................... None
See application file for complete search history.

(56) References Cited

U.S. PATENT DOCUMENTS 6,137,038 A * 10/2000 Vattikonda ............... 800/320.1
6,551,962 B1 * 4/2003 Pershing et al. ............. 504/100

OTHER PUBLICATIONS

Grant et al (2003, J. Dairy Sci. 86:1707-1715).*
Mitchell (May 2002, Yield Benefit of Corn event Mon 863, In: Faculty Paper Series, Department of Agricultural Economics, Texas A&M University).*

* cited by examiner

*Primary Examiner*—Anne Kubelik
(74) *Attorney, Agent, or Firm*—Timothy K. Ball, Esq.; Howrey LLP (57) ABSTRACT

The present invention provides compositions and methods for detecting the presence of the corn event MON863 DNA inserted into the corn genome from the transformation of the recombinant construct containing a Cry3Bb gene and of genomic sequences flanking the insertion site. The present invention also provides the corn event MON863 plants, progeny and seeds thereof that contain the corn event MON863 DNA.

11 Claims, 2 Drawing Sheets

CORN EVENT PV-ZMIR13 (MON863) PLANTS AND COMPOSITIONS AND METHODS FOR DETECTION THEREOF

CROSS REFERENCE TO RELATED APPLICATIONS

This application is a 35USC§371 application of PCT/US03/22860, filed Jul. 23, 2003, which claims the benefit of priority to U.S. Provisional Application 60/399,279, filed Jul. 29, 2002.

FIELD OF THE INVENTION

The present invention relates to the field of plant molecular biology. The invention more specifically relates to a coleopteran resistant corn plant (*Zea mays*) PV-ZMIR13, designated MON863, and to seeds and progeny of the corn plant MON863. The corn plant MON863 and its progeny are particularly resistant to *Diabrotica vergifera, Diabrotica undecimpunctata*, and *Leptinotarsa decemlineata*.

The present invention more specifically also relates to a DNA construct inserted into the corn plant genome in event MON863 for conferring resistance to insect infestation by a coleopteran species. The present invention also relates to assays for detecting the presence of a corn plant MON863 DNA in a sample and compositions thereof.

BACKGROUND OF THE INVENTION

Corn is an important crop and is a primary food source in many areas of the world. The methods of biotechnology have been applied to corn plants for improvement of the agronomic traits and the quality of the product. Expression of foreign genes in plants is known to be influenced by their chromosomal position, perhaps due to chromatin structures (e.g., heterochromatin) or the proximity of transcriptional regulation elements (e.g., enhancers) close to the integration site (Weising et al., Ann. Rev. Genet 22:421-477, 1988). For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the premarket approval and labeling of food derived from recombinant crop plants, for example. It is possible to detect the presence of a transgene by any well-known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different events, particularly those produced using the same DNA construct unless the sequence of chromosomal DNA adjacent to the inserted DNA ("flanking DNA") is known. An event-specific PCR assay is discussed, for example, by Windels et al. (Med. Fac. Landbouww, Univ. Gent 64/5b: 459-462, 1999), who identified glyphosate tolerant soybean event 40-3-2 by PCR using a primer set spanning the junction between the insert and flanking DNA, specifically one primer that included sequence from the insert and a second primer that included sequence from flanking DNA.

SUMMARY OF THE INVENTION

According to one preferred embodiment of the present invention, compositions and methods are provided for detecting the presence of the transgene/genomic insertion region from a novel corn plant PV-ZMIR13, designated MON863. DNA sequences are provided that comprise at least one junction sequence of MON863 selected from the group consisting of SEQ ID NO:1 (arbitrarily assigned 5' end insert-to-genome junction) and SEQ ID NO:2 (arbitrarily assigned 3' end insert-to-genome junction) and complements thereof, wherein the junction sequence spans the junction between a heterologous DNA inserted into the corn genome and the DNA from the corn cell flanking the insertion site and is diagnostic for the event.

According to another preferred embodiment of the present invention, DNA sequences that comprise the novel transgene/genomic insertion region, SEQ ID NO:3 (sequence containing the arbitrarily assigned 5' end of the inserted DNA) and SEQ ID NO:4 (sequence containing the arbitrarily assigned 3' end of the inserted DNA) for example, are disclosed.

According to still another preferred embodiment of the present invention, the DNA sequences that comprise at least from about 11 to about 50 or more nucleotides of the 5' transgene portion of the DNA sequence of SEQ ID NO:7 and a similar length of 5' flanking corn DNA sequence of SEQ ID NO:5, or a similar length of 3' transgene portion of the DNA sequence of SEQ ID NO:8 and a similar length of 3' flanking corn DNA of SEQ ID NO:6, for use as DNA primers in DNA amplification methods are also disclosed in the present invention. Amplicons produced using these primers are diagnostic for corn event MON863. An amplicon produced by a first DNA primer homologous or complementary to SEQ ID NO:7 coupled with a second DNA primer homologous or complementary to SEQ ID NO:5, when both are present together in a reaction mixture with corn event MON863 DNA in a sample are an aspect of the present invention. An amplicon produced by a third DNA primer homologous or complementary to SEQ ID NO:8 coupled with a fourth DNA primer homologous or complementary to SEQ ID NO:6, when both are present together in a reaction mixture with corn event MON863 DNA in a sample, are another aspect of the present invention. The corn plant MON863 and progeny derived therefrom that contain these DNA sequences used in a DNA amplification reaction to provide one or more diagnostic amplicons are aspects of the invention.

According to yet another preferred embodiment of the present invention, methods of detecting the presence of a DNA corresponding to the corn event MON863 event in a sample are provided. Such methods comprise the steps of: (a)

contacting a biological sample suspected of containing an event MON863 DNA with a primer pair that, when used in a nucleic acid amplification reaction with said DNA, produces an amplicon that is diagnostic for the corn event MON863; (b) performing a nucleic acid amplification reaction, thereby producing the amplicon; and (c) detecting the amplicon. The amplicons specifically exemplified herein correspond to a first amplicon of about 508 base pairs as set forth in SEQ ID NO:3 and a second amplicon of about 584 base pairs as set forth in SEQ ID NO:4, or longer or shorter amplicons, wherein said first amplicon contains as least a nucleotide sequence corresponding to SEQ ID NO:1 from about nucleotide 1 through about nucleotide 11 or from about nucleotide 10 through about nucleotide 20 and said second amplicon contains at least a nucleotide sequence corresponding to SEQ ID NO:2 from about nucleotide 1 through about nucleotide 11 or from about nucleotide 10 through about nucleotide 20.

According to yet another preferred embodiment of the present invention, methods of detecting the presence of a DNA corresponding to the MON863 event in a sample are provided. Such methods comprise the steps of: (a) contacting a biological sample suspected of containing an event MON863 DNA with a probe that hybridizes under stringent hybridization conditions with said DNA and that does not hybridize under stringent hybridization conditions with DNA from a control corn plant that does not contain an inserted DNA derived from pMON25097; (b) subjecting the sample and the probe to stringent hybridization conditions; and (c) detecting hybridization of the probe to the genomic DNA, wherein detection of probe binding to said DNA is diagnostic for the presence of event MON863 DNA in said sample.

According to a further preferred embodiment of the present invention, there is provided a novel corn plant MON863, that comprises DNA sequences comprising the novel transgene/genomic insertion regions as set forth in SEQ ID NO:3 and SEQ ID NO:4. The seeds of the plants of MON863, the progeny of the plants of MON863 and the methods for producing a corn plant by crossing the corn plant MON863 with itself or with another corn plant are further embodiments of the present invention.

The foregoing and other preferred embodiments of the present invention will become more apparent from the following detailed descriptions.

BRIEF DESCRIPTION OF THE DRAWINGS AND SEQUENCES

Description of Drawings

FIG. 2 is a graphical map illustrating the general organization of the elements comprising the heterologous nucleic acid sequences inserted into the corn event MON863 genome and essentially sets forth the positions at which the inserted nucleic acid sequences are linked to corn genomic DNA sequences designated herein as corn genomic nucleic acid sequences which flank the ends of the inserted heterologous DNA sequences; the corn event MON863 being characterized as follows: corn genomic DNA [1] flanking the arbitrarily assigned 5' end of the full length primary functional inserted DNA sequence is adjacent to a non-naturally occurring CaMV35S AS4 promoter sequence [2] (P-CaMV.AS4, SEQ ID NO:17) operably connected to a wheat chlorophyll A/B binding protein untranslated leader sequence [3] (L-Ta.hcb1, SEQ ID NO:18) operably connected to a rice actin intron sequence [4] (I-Os.Act1, SEQ ID NO:19) operably connected to a non-naturally occurring sequence encoding Cry3Bb variant protein [5] (SEQ ID NO:20) operably connected to a wheat heat shock Hsp17 transcription termination and polyadenylation sequence [6](T-Ta.Hsp17, SEQ ID NO:21), and the full-length primary functional inserted DNA sequence being flanked by the corn genomic DNA at the arbitrarily assigned 3' end [7], in which the junction between [1] and [2] ([8]) corresponds to SEQ ID NO:1, and the junction between [6] and [7] ([9]) corresponds to SEQ ID NO:2.

DESCRIPTION OF SEQUENCES

SEQ ID NO:1 corresponds to a junction sequence between corn genome and inserted DNA that is diagnostic for the arbitrarily assigned 5' end of the full-length primary functional inserted DNA sequence in the corn event MON863.

SEQ ID NO:2 corresponds to a junction sequence between corn genome and inserted DNA that is diagnostic for the arbitrarily assigned 3' end of the full-length primary functional inserted DNA sequence in the corn event MON863.

Figure 2:
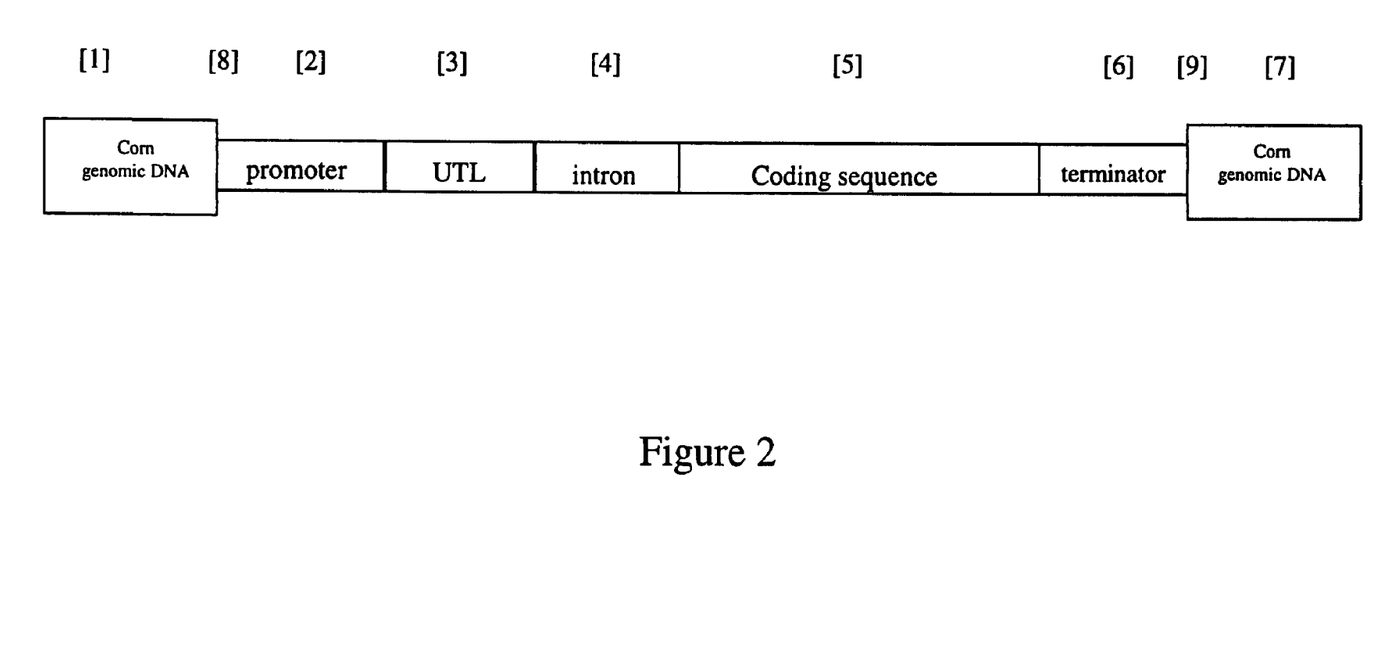

SEQ ID NO:3 corresponds to the sequences represented substantially by [1] and [2] of FIG. 2.

SEQ ID NO:4 corresponds to the sequences represented substantially by [6] and [7] of FIG. 2.

SEQ ID NO:5 corresponds to the partial corn genome DNA sequence that is adjacent to and flanking the 5' end of the arbitrarily assigned 5' end of the partial Cry3Bb DNA coding sequence inserted in the corn event MON863.

SEQ ID NO:6 corresponds to the partial corn genome DNA sequence that is adjacent to and flanking the 3' end of the arbitrarily assigned 3' end of the partial Cry3Bb DNA coding sequence inserted in the corn event MON863.

SEQ ID NO:7 corresponds to the sequence of the arbitrarily assigned 5' end of the partial Cry3Bb DNA coding sequence inserted in the corn event MON863.

SEQ ID NO:8 corresponds to the sequence of the arbitrarily assigned 3' end of the partial Cry3Bb DNA coding sequence inserted in the corn event MON863.

SEQ ID NO:9 corresponds to a 5' primer sequence (primer A) complementary to a part of the corn genomic DNA sequence identified as flanking the arbitrarily assigned 5' end of the full length primary functional inserted DNA sequence in the corn event MON863, and when paired with a primer corresponding to the reverse complement of the sequence set forth in SEQ ID NO:10 and template DNA of the corn event MON863, produces an amplicon comprising SEQ ID NO:3 that is diagnostic for the corn event MON863 DNA in a sample.

SEQ ID NO:10 corresponds to the reverse complement of a 3' primer sequence (primer B) complementary to a part of the arbitrarily assigned 5' end sequence of the full length primary functional DNA inserted into the corn genome in the corn event MON863, and when paired with a primer corresponding to the sequence set forth in SEQ ID NO:9 and template DNA of the corn event MON863, produces an amplicon comprising SEQ ID NO:3 that is diagnostic for the corn event MON863 DNA in a sample.

SEQ ID NO:11 corresponds to a 5' primer sequence (primer C) complementary to part of the arbitrarily assigned 3' end sequence of the full length primary functional DNA inserted into the corn genome in the corn event MON863, and when paired with a primer corresponding to the reverse complement of the sequence set forth in SEQ ID NO:12 and template DNA of the corn event MON863, produces an amplicon having SEQ ID NO:4 that is diagnostic for the corn event MON863 DNA in a sample.

SEQ ID NO:12 corresponds to the reverse complement of a 3' primer sequence (primer D) complementary to a part of the corn genomic DNA sequence identified as flanking the arbitrarily assigned 3' end of the full length primary functional inserted DNA sequence in corn event MON863, and when paired with a primer corresponding to the sequence set forth in SEQ ID NO:11 and the template DNA of the corn event MON863, produces an amplicon having SEQ ID NO:4 that is diagnostic for corn event MON863 DNA in a sample.

SEQ ID NO:13 corresponds to a 5' genome walker primer 1.

SEQ ID NO:14 corresponds to a 5' genome walker primer 2.

SEQ ID NO:15 corresponds to a 3' genome walker primer 1.

SEQ ID NO:16 corresponds to a 3' genome walker primer 2.

SEQ ID NO:17 corresponds to CaMV35S AS4 promoter sequence.

SEQ ID NO:18 corresponds to a wheat chlorophyll A/B binding protein untranslated leader sequence (L-Ta.hcb1).

SEQ ID NO:19 corresponds to a rice actin intron sequence (I-Os.Act1).

SEQ ID NO:20 corresponds to a non-naturally occurring sequence encoding a Cry3Bb variant protein.

SEQ ID NO:21 corresponds to wheat heat shock Hsp17 transcription termination and polyadenylation sequence (T-Ta.Hsp17).

DETAILED DESCRIPTION OF THE PREFERRED EMBODIMENTS

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, Genes V, Oxford University Press: New York, 1994. The nomenclature for DNA bases as set forth at 37 CFR § 1.822 is used.

As used herein, the term "biological sample", or "sample", is intended to include nucleic acids, polynucleotides, DNA, RNA, tRNA, cDNA, and the like in a composition or fixed to a substrate which enables the sample to be subjected to molecular probe analysis or thermal amplification using oligonucleotide probes and/or primers.

As used herein, the term "corn" means *Zea mays* or *maize* and includes all plant varieties that can be bred with corn, including wild maize species.

As used herein, the term "comprising" means "including but not limited to".

As used herein, the term "diagnostic" refers to the fact that, for the purposes of identifying nucleic acid sequences as those contained within or derived from the corn event MON863, any one or more of the novel DNA sequences set forth herein comprise the corn genome flanking sequences adjacent to and linked to the arbitrarily assigned ends of the inserted heterologous DNA sequences are necessary and sufficient as being descriptive as a distinguishing characteristic of the corn event MON863 genome, so long as the sequence comprises at least a part of one of the ends of the inserted heterologous DNA sequence or the corn genome sequence flanking or adjacent to one of these ends and includes at least the two nucleotides, the di-nucleotide, comprising the point at which the corn genome sequence and the inserted heterologous DNA sequence are linked together by a phosphodiester bond. It is well known in the art that a sequence which is diagnostic for a particular event, such as those disclosed herein for the corn event MON863, which is not present in a particular sample containing corn genome nucleic acids, is indicative that the sample does not contain the diagnostic sequence and therefore the nucleic acids in the sample are not or were not derived from and have not been contained within the genome of the corn event MON863. In addition, additional novel and diagnostic sequences are present within the corn event MON863 DNA as exemplified herein selected from the group consisting of SEQ ID NO:1, SEQ ID NO:2, SEQ ID NO:3, and SEQ ID NO:4 and complements thereof.

A transgenic "event" is produced by transformation of plant cells with a heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous DNA. Even after repeated backcrossing to a recurrent parent, the inserted DNA and flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

It is also to be understood that two different transgenic plants can also be mated to produce offspring that contain two or more independently segregating exogenous genes (exogenous genes referring nucleotide sequences that are not naturally occurring in the plant genome, i.e., heterogeneous to the corn plant). Selfing of appropriate progeny can produce plants that are homozygous for any combination of the exogenous genes. Backcrossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987).

A "probe" is an isolated nucleic acid to which a conventional detectable label or reporter molecule, e.g., a radioactive isotope, ligand, chemiluminescent agent, or enzyme may be linked or attached. Such a probe is complementary to a sequence within a target nucleic acid, in the case of the present invention, to a sequence of genomic DNA from the corn event MON863 whether from a corn plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acid probes that are annealed to, for any given single primer, a complementary target DNA sequence by nucleic acid hybridization to form a hybrid between the primer and the target DNA sequence, and then extended along the target DNA strand by a polymerase, e.g., a DNA polymerase. Primer pairs of the present invention refer to two or more different primer sequences for is in amplification of a nucleic acid sequence that is between and linked to the target sequences designated as the reverse complement or substantially the reverse complement of the primers, e.g., by the polymerase chain reaction (PCR) or other conventional nucleic-acid amplification methods.

Probes and primers are generally from about 11 nucleotides or more in length, preferably from about 18 nucleotides or more in length, more preferably from about 24 nucleotides or more in length, and most preferably from about 30 nucleotides or more in length. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology,* ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications,* Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Primers and probes constructed based on the flanking DNA, insert sequences, and junction sequences disclosed herein can be used to confirm the presence of the disclosed sequences in a sample by conventional methods, e.g., by recloning and sequencing such sequences.

Any single nucleic acid probe or primer of the present invention hybridizes under stringent conditions to a specific target DNA sequence. Any conventional nucleic acid hybridization or amplification method can be used to identify the presence of DNA from a transgenic event in a sample. Nucleic acid molecules or fragments thereof specifically hybridize to other nucleic acid molecules under certain circumstances. As used herein, two different nucleic acid molecules each comprising different sequences, are said to specifically hybridize to one another if the two molecules form an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they hybridize to one another with sufficient stability to permit them to remain annealed to one another under conventional "high-stringency" conditions. Conventional stringency conditions are described by Sambrook et al., 1989, and by Haymes et al. (In: *Nucleic Acid Hybridization, A Practical Approach*, IRL Press, Washington, D.C., 1985). Departures from complete complementarity are therefore permissible, as long as such departures do not completely preclude the capacity of the molecules to form a double-stranded structure. In order for a nucleic acid molecule to serve as a primer or probe it needs only be sufficiently complementary in sequence to be able to form a stable double-stranded structure under the particular solvent and salt concentrations employed.

The term "specific for (a target sequence)" indicates that a probe or primer hybridizes under stringent hybridization conditions only to the target sequence in a sample comprising the target sequence, and that the hybridization is detectable.

As used herein, an "isolated" nucleic acid is one that has been substantially separated or purified away from other nucleic acid sequences in the cell of the organism in which the nucleic acid naturally occurs, i.e., other chromosomal and extrachromosomal DNA and RNA, by conventional nucleic acid-purification methods. The term also embraces recombinant nucleic acids and chemically synthesized nucleic acids.

As used herein, a "substantially homologous" sequence is a nucleic acid sequence that specifically hybridizes to the complement of the nucleic acid sequence to which it is being compared, i.e., the target sequence, under high stringency conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y., 6.3.1-6.3.6., 1989. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a nucleic acid of the present invention will specifically hybridize to one or more of the nucleic acid molecules set forth either in SEQ ID NO:1 or SEQ ID NO:2 or complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth either in SEQ ID NO:1 or SEQ ID NO:2 or complements or fragments of either under high stringency conditions. A nucleic acid of the present invention that hybridizes to a nucleic acid sequence comprising SEQ ID NO:1 or to a nucleic acid sequence comprising SEQ ID NO:3 will not necessarily hybridize to a nucleic acid sequence comprising SEQ ID NO:2 or to a nucleic acid sequence comprising SEQ ID NO:4, and vice versa.

In one aspect of the present invention, a preferred marker nucleic acid molecule of the present invention has the nucleic acid sequence set forth in SEQ ID NO:1 or in SEQ ID NO:2 or complements thereof or fragments of either. In another aspect of the present invention, a preferred marker nucleic acid molecule of the present invention shares between 80% and 100% or between 90% and 100% sequence identity with the nucleic acid sequence set forth in SEQ ID NO:1 and SEQ ID NO:2 or complement thereof or fragments of either. In a further aspect of the present invention, a preferred marker nucleic acid molecule of the present invention shares between 95% and 100% sequence identity with the sequence set forth in SEQ ID NO:1 and SEQ ID NO:2 or complement thereof or fragments of either. SEQ ID NO:1 and SEQ ID NO:2 may be used as markers in plant breeding methods to identify the progeny of genetic crosses similar to the methods described for simple sequence repeat DNA marker analysis, in "*DNA markers: Protocols, Applications, and Overviews,* 173-185, Cregan, et al., eds., Wiley-Liss NY, 1997. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the individual primers in a primer pair to hybridize only to the individual and unique target nucleic-acid sequence to which each primer, comprising the corresponding wild-type sequence (or its complement), would bind, and preferably to produce a unique amplification product, the amplicon, in a DNA thermal amplification reaction.

As used herein, the term "transformation" refers to the transfer of a nucleic acid fragment into the genome of a host organism such as a host plant, resulting in genetically stable inheritance. Host plants containing the transformed nucleic acid fragments are referred to as "transgenic plants".

As used herein, "amplified DNA" or "amplicon" refers to the product of nucleic-acid amplification of a target nucleic acid sequence that is part of a nucleic acid template. For example, to determine whether the corn plant resulting from a sexual cross contains transgenic event genomic DNA from the corn plant MON863 of the present invention, DNA extracted from a corn plant tissue sample may be subjected to a nucleic acid amplification method using a primer pair that includes a primer derived from the flanking sequence in the genome of the plant adjacent to the insertion site of the inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, preferably plus about fifty nucleotide base pairs, more preferably plus about two hundred-fifty nucleotide base pairs, and even more preferably plus about four hundred-fifty nucleotide base pairs. Alternatively, a primer pair can be derived from the flanking sequence on both sides of the inserted DNA so as to produce an amplicon that includes the entire insert nucleotide sequence. A member of a primer pair derived from the plant genomic sequence may be located in a distance from the inserted DNA sequence, this distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications,* ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or the flanking sequence from the corn event MON863 can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. One such method is Genetic Bit Analysis (Nikiforov, et al. Nucleic Acid Res. 22:4167-4175, 1994) where a DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. The light signal indicates the presence of the transgene insert/flanking sequence due to successful amplification, hybridization, and single or multi-base extension.

Fluorescence Polarization as described by Chen, et al., (Genome Res. 9: 492-498, 1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. A single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al. (Nature Biotech. 14: 303-308, 1996). Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. The fluorescent signal indicates the presence of the flanking/transgene insert sequence due to successful amplification and hybridization, and is diagnostic for the corn event MON863 nucleic acid in a sample.

All of the above methods can be modified to determine the zygosity of a particular sample of nucleic acids derived from a single source. For example, a corn event MON863 plant which is homozygous for the event 863 allele contains within its genome two copies of the event 863 allele characteristic of and diagnostic for the corn event MON863 genome, and thus when selfed would breed true. Alternatively, a corn event MON863 homozygous plant can be crossed with another variety of corn, and the result of that cross would be plants that were heterozygous for the event MON863 allele. Methods are envisioned in which one skilled in the art could determine the zygosity of a particular plant with reference to the event MON863 allele.

For example, the use of three different primers in an amplification reaction with corn event MON863 DNA as a template, and in a separate and parallel amplification reaction with negative control corn DNA that is not MON863, i.e., that does not contain the inserted DNA present within MON863 DNA, would result in two different outcomes depending on the zygosity of the corn DNA containing the corn event MON863 DNA. Exemplary primers could be selected from the group consisting of SEQ ID NO:9, SEQ ID NO:10, and SEQ ID NO:12. Amplification of non-MON863 DNA with this group of primers would result in primer pair SEQ ID NO:10 and SEQ ID NO:12 producing a first amplicon corresponding to the contiguous corn genome sequence into which the PV-ZMIR13 sequence was inserted, that amplified sequence corresponding substantially to the linked combination of SEQ ID NO:5 and SEQ ID NO:6. This first amplicon would be expected in a plant that was heterozygous for the corn event MON863 allele, however, a heterozygote would also produce a second amplicon corresponding to SEQ ID NO:3 from the extension of the primer pair corresponding to SEQ ID NO:9 and SEQ ID NO:10. A corn plant containing DNA that was homozygous for the MON863 allele would only produce the second amplicon.

Similarly, a third amplicon would be produced from a thermal amplification reaction that used the primers SEQ ID NO:10, SEQ ID NO:11, and SEQ ID NO:12 with template DNA from a MON863 corn plant, this third amplicon corresponding to SEQ ID NO:4. This third amplicon would be the only amplicon produced using this particular combination of primers and template DNA if the plant was homozygous for the MON863 allele, however, heterozygote template DNA would result in the amplification of the first and the third amplicons, and non-MON863 template DNA would result in the amplification of only the first amplicon.

Herein, the inventors have determined as judged by molecular characterization that corn event MON863 contains a primary functional insert containing a significant portion of the transformation plasmid, PV-ZMIR13. This segment is detectable and diagnostic for the event MON863 nucleic acid sequences in a sample, in particular in plants that have been selfed since the origination of the MON863 event.

There are many methods for transforming the Cry3Bb nucleic acid molecules into plant cells such as maize plant cells to produce a desired event such as MON863. Suitable methods are believed to include virtually any methods by which nucleic acid molecules may be introduced into the cells, such as by *Agrobacterium* infection or direct delivery of nucleic acid molecules that may include PEG-mediated transformation, electroporation and acceleration of DNA coated particles, etc. (Pottykus, Ann. Rev. Plant Physiol. Plant Mol. Biol. 42:205-225, 1991; Vasil, Plant Mol. Biol. 25: 925-937, 1994). For example, electroporation has been used to transform *Zea mays* protoplasts (Fromm et al., Nature 312:791-793, 1986). In general, the following are four most commonly used general methods for delivering a gene into cells: (1) chemical methods (Graham and van der Eb, Virology, 54:536-539, 1973); (2) physical methods such as microinjection (Capecchi, Cell 22:479-488, 1980), electroporation (Wong and Neumann, Biochem. Biophys. Res. Commun. 107:584-587, 1982; Fromm et al., Proc. Natl. Acad. Sci. (USA) 82:5824-5828, 1985; U.S. Pat. No. 5,384,253); and the gene gun (Johnston and Tang, Methods Cell Biol. 43:353-365, 1994); (3) viral vectors (Clapp, Clin. Perinatol. 20:155-168, 1993; Lu et al., J. Exp. Med. 178:2089-2096, 1993; Eglitis and Anderson, Biotechniques 6:608-614, 1988); and (4) receptor-mediated mechanisms (Curiel et al., Hum. Gen. Ther. 3: 147-154, 1992; Wagner et al., Proc. Natl. Acad. Sci. (USA) 89: 6099-6103, 1992).

Transformation of plant protoplasts can be achieved using methods based on calcium phosphate precipitation, polyethylene glycol treatment, electroporation, and combinations of these treatments. See for example (Potrykus et al., Mol. Gen. Genet., 205:193-200, 1986; Lorz et al., Mol. Gen. Genet., 199:178, 1985; Fromm et al., Nature, 319:791, 1986; Uchimiya et al., Mol. Gen. Genet.:204:204, 1986; Callis et al., Genes and Development, 1183, 1987; Marcotte et al., Nature, 335:454, 1988). Application of these systems to different plant strains depends upon the ability to regenerate that particular plant strain from protoplasts. Among them are the methods for corn (U.S. Pat. No. 5,569,834, U.S. Pat. No. 5,416,011; McCabe et al., Biotechnology 6:923, 1988; Christou et al., Plant Physiol., 87:671-674, 1988). Illustrative methods for the regeneration of cereals from protoplasts are also described (Fujimura et al., Plant Tissue Culture Letters, 2:74, 1985; Toriyama et al., Theor. Appl. Genet. 205:34, 1986; Yamada et al., Plant Cell Rep. 4: 85, 1986; Abdullah et al., Biotechnology, 4:1087, 1986).

A transgenic plant such as a transgenic corn MON863 plant formed using transformation methods typically contains a single added Cry3Bb gene on one chromosome. Such a transgenic plant can be referred to as being heterozygous for the added Cry3Bb gene. More preferred is a transgenic plant that is homozygous for the added Cry3Bb gene; i.e., a transgenic plant that contains two added Cry3Bb genes, one gene at the same locus on each chromosome of a chromosome pair. A homozygous transgenic plant can be obtained by sexually mating (selfing) an independent segregated transgenic plant that contains a single added Cry3Bb gene, germinating some of the seeds produced and analyzing the resulting plants produced for the Cry3Bb gene.

It is understood that two different transgenic plants can also be mated to produce offspring that contain two independently segregating added Cry3Bb genes. Selfing of appropriate progeny can produce plants that are homozygous for both added Cry3Bb genes that encode Cry3Bb polypeptides.

Backcrossing to a parental plant and out-crossing with a non-transgenic plant are also contemplated, as is vegetative propagation.

Specifically, a method for producing a corn plant that is resistant to coleopteran insect infestation may be conducted with the following steps: 1) sexually crossing a first corn plant grown from the corn seed event MON863 comprising a DNA molecule selected from the group consisting of SEQ ID NO: 1, SEQ ID NO:2, SEQ ID NO:3, SEQ ID NO:4 and SEQ ID NO:20 that confers resistance to coleopteran insect infestation, and a second corn plant that lacks the resistance to coleopteran insect infestation, thereby producing a plurality of first progeny plants; 2) selecting a first progeny plant that is resistant to coleopteran insect infestation; 3) selfing said first progeny plant, thereby producing a plurality of second progeny plants; and 4) selecting from said second progeny plants a plant resistant to coleopteran insect infestation. The first progeny plant that is resistant to coleopteran insect infestation or the second progeny plant that is resistant to coleopteran insect infestation may be backcrossed to the second corn plant or a third corn plant resulting in a corn plant that is resistant to coleopteran insect damage infestation.

The regeneration, development, and cultivation of plants such as the MON863 plants from transformants or from various transformed explants are well known in the art (Weissbach and Weissbach, In: *Methods for Plant Molecular Biology*, Eds., Academic Press, Inc. San Diego, Calif., 1988). This regeneration and growth process may typically include the steps of selection of transformed cells containing exogenous Cry3Bb genes, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The regeneration of plants containing the foreign, exogenous gene that encodes a protein of interest is well known in the art. As described in the present invention, the regenerated plants such as the regenerated MON863 plants that contain the Cry3Bb nucleic acids, either wild type or chemically synthesized, that encode for the Cry3Bb proteins, may be preferably self-pollinated to provide homozygous transgenic maize plants, as discussed before. Otherwise, pollen obtained from the regenerated maize plants may be crossed to seed-grown plants of agronomically important lines. Conversely, pollen from plants of these important lines is used to pollinate regenerated plants. A transgenic MON863 plant of the present invention may be cultivated using methods well known to one skilled in the art.

There are a variety of methods for the regeneration of plants from plant tissue. The particular method of regeneration will depend on the starting plant tissue and the particular plant species to be regenerated. Transformation of monocot plants using electroporation, particle bombardment, and *Agrobacterium* has also been reported. Transformation and plant regeneration have been achieved in many monocot plants that include maize, asparagus, barley and wheat, etc. (Bytebier et al., Proc. Natl. Acad. Sci. USA 84:5345, 1987; Wan and Lemaux, Plant Physiol 104:37, 1994; Rhodes et al., Science 240: 204, 1988; Gordon-Kamm et al., Plant Cell, 2:603, 1990; Fromm et al., Bio/Technology 8:833, 1990; Armstrong et al., Crop Science 35:550-557, 1995; Vasil et al., Bio/Technology 10:667, 1992; U.S. Pat. No. 5,631,152).

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones (see, for example, Sambrook et al., Molecular Cloning: A Laboratory Manual, Cold Spring Harbor Press, 1989; Mailga et al., Methods in Plant Molecular Biology, Cold Spring Harbor Press, 1995; Birren et al., Genome Analysis: Analyzing DNA, 1, Cold Spring Harbor, N.Y., 1997).

DNA detection kits can be developed using the compositions disclosed herein and the methods well known in the art of DNA detection. The kits are useful for identification of corn event MON863 DNA in a sample and can be applied to methods for breeding corn plants containing the MON863 DNA. The kits contain one or more DNA sequences comprising at least 11 contiguous nucleotides homologous or complementary to sequences selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and complements thereof. These DNA sequences can be used in DNA amplification reactions or as probes in a DNA hybridization method.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Figure 1:
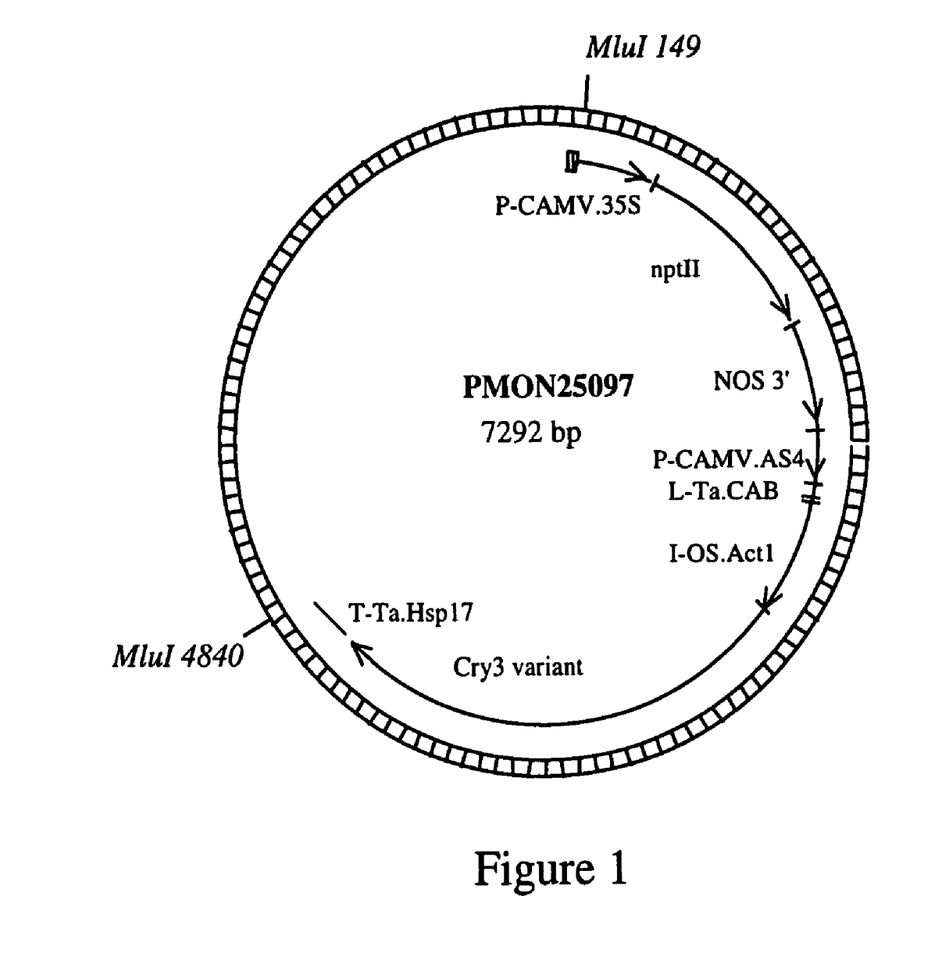
FIG. 1 illustrates a plant expression vector PV-ZMIR13, also designated herein as pMON25097, from which the corn rootworm event MON863 is generated through particle acceleration technology using a Mlu I restriction fragment from about nucleotide position 149 through about nucleotide position 4840.

Isolation and Characterization of the DNA Sequences Flanking the MON863 Insertion Event Corn event MON863 was generated through particle acceleration technology using a 4.7-Kb agarose gel-isolated Mlu I restriction fragment from the plasmid vector PV-ZMIR13 (pMON25097, FIG. 1). The plant expression vector pMON25097 contains a first expression cassette comprising a non-naturally occurring CaMV35S AS4 promoter sequence (P-CaMV.AS4, SEQ ID NO:17) operably connected to a wheat chlorophyll A/B binding protein untranslated leader sequence (L-Ta.hcb1, SEQ ID NO:18) operably connected to a rice actin intron sequence (I-Os.Act1, SEQ ID NO:19) operably connected to a non-naturally occurring sequence encoding Cry3Bb variant protein (SEQ ID NO:20) operably connected to a wheat heat shock Hsp17 transcription termination and polyadenylation sequence (T-Ta.Hsp17, SEQ ID NO:21). The plant expression vector pMON25097 contains a second expression cassette linked to the Cry3Bb expression cassette that confers paromomycin resistance to transformed plant tissue (i.e. the 3' end of the cry3Bb expression cassette is linked to the 5' end of the second expression cassette conferring paromomycin resistance). This resistance cassette consists of an enhanced CaMV35S promoter sequence (U.S. Pat. No. 5,164,316) that is operably connected to a neomycin phosphotransferase coding sequence (U.S. Pat. No. 5,569,834) that is operably connected to a nopaline synthase transcription termination and polyadenylation sequence (Fraley et al. Proc. Natl. Acad. Sci. USA 80:4803-4807, 1983). Transgenic corn plants resistant to paromomycin were derived essentially as described in U.S. Pat. No. 5,424,412.

Molecular characterization of the insert in the corn event MON863 demonstrated that one copy of the DNA fragment used for transformation is present in the corn event MON863. In order to develop event-specific PCR identification methods, the sequences of corn DNA flanking the 5' and 3' ends of the insert in the corn event MON863 were determined using GenomeWalker™ technology (Clontech Laboratories, Inc.) in accordance with the manufacturer's instructions. The GenomeWalker™ method involves first completely digesting purified corn MON863 DNA with different restriction enzymes provided in the GenomeWalker™ kit that leave blunt ends. Next, the purified blunt-ended genomic DNA fragments are ligated to GenomeWalker™ Adaptors comprising known nucleic acid fragments. Each ligation is then amplified in a first PCR reaction using an outer adaptor primer, SEQ ID NO:22 (5'-GTAATACGACTCACTATAGGGC-3') provided by GenomeWalker™ and an outer, gene-specific primer (SEQ ID NO:13, 5'-GAACGTCTTCTTTTTCCACGATGCTCC-3', and SEQ ID NO:15, 5'-GCGAGTCTGATGAGACATCTCTGTAT-3', for the 5' and 3' ends of the transgene insert, respectively). The first PCR product mixture is then diluted and used as a template for a secondary or nested PCR with the nested adaptor primer, SEQ ID NO:23 (5'-ACTATAGGGCACGCGTGGT-3') provided by GenomeWalker™ and a nested gene-specific primer (SEQ ID NO:14, 5'-TCGGCAGAGGCATCTTGAATGATAGC-3', and SEQ ID NO:16, 5'-AATTTGGTTGATGTGTGTGCGAGTTCT-3', for the 5' and 3' ends of the transgene insert, respectively). The secondary PCR product, which begins with the known gene-specific sequences and extends into the unknown adjacent genomic DNA, can then be sequenced using methods well known in the art. Once the flanking corn genomic sequences were determined, PCR assays capable of detecting the presence of corn plant PV-ZMIR13 (MON863) DNA in a sample were developed.

Following this procedure, the nucleotide sequence as set forth in SEQ ID NO:5 was characterized as the corn genome sequence that is immediately adjacent to and upstream of the arbitrarily assigned 5' end of the pMON25097 DNA fragment that was inserted into the corn genome resulting in the construction and isolation of transgenic corn event MON863. One skilled in the art, or even one of ordinary skill in the art, would realize that additional nucleotide sequence information can readily be obtained that is even more distal from the junction sequence as set forth in SEQ ID NO:1 but still within the corn genome than the present 242 nucleotides exemplified herein in SEQ ID NO:5, and from nucleotide position 267 through nucleotide position 508 as set forth in SEQ ID NO:3. Also, the nucleotide sequence as set forth in SEQ ID NO:6 was characterized as the corn genome sequence that is immediately adjacent to and downstream of the arbitrarily assigned 3' end of the pMON25097 DNA fragment that was inserted into the corn genome resulting in the construction and isolation of transgenic corn event MON863. One skilled in the art will also realize that additional nucleotide sequence information can readily be obtained that is even more distal from the junction sequence as set forth in SEQ ID NO:2 but still within the corn genome than the present 224 nucleotides exemplified herein in SEQ ID NO:6, and from nucleotide position 361 through nucleotide position 584 as set forth in SEQ ID NO:4.

Example 2

Detection of the Presence of MON863 DNA in a Sample

The following provides a non-limiting example of the PCR assays developed to detect the presence of the MON863 DNA in a sample.

DNA was extracted from approximately 100 mg of ground grain tissue using Qiagen's Dneasy Plant Mini Kit (catalog # 68163, Valencia, Calif.) according to the manufacturer's recommended protocol with one exception. The grain used was processed prior to extraction in a −80° C. freezer, and not ground under liquid nitrogen using a mortar and pestle immediately prior to extraction. DNA quantitation was conducted using methods well-known in the art, a Hoefer DNA Quant 200 Fluorometer, and Boehringer Mannheim (Indianapolis, Ind.) molecular size marker IX as a DNA calibration standard.

PCR analysis of the genomic DNA sequences flanking the 5' end of the insert in MON863 was performed using one primer (primer A) derived from the 5' genomic flanking sequence (SEQ ID NO:9, 5'-GTCTTGCGAAGGATAGTGGGAT-3') paired with a second primer (primer B) located near the 5' end of the inserted DNA in the 35S promoter (SEQ ID NO:10, 5'-CATATGACATAAGCGCTCTTGG-3'), covering a 508-bp region. The PCR analysis for genomic DNA sequences flanking the 3' end of the MON863 insert was conducted using one primer (primer D) derived from the 3' genomic flanking sequence (SEQ ID NO:12, 5'-AGACTCTATGCTCTGCTCATAT-3') paired with a second primer (primer C) located in the tahsp17 polyadenylation sequence near the 3' end of the insert spanning a 584-bp region (SEQ ID NO:11, 5'-CTGATCATTGGTGCTGAGTCCTT-3') (FIG. 2). The PCR analyses were conducted using 50 ng of the corn event MON863 genomic DNA or a MON846 non-transgenic genomic DNA template in a 50 µL reaction volume containing a final concentration of 1.5 mM Mg$^{2+}$, 0.4 µM of each primer, 200 µM each dNTP, and 2.5 units of Taq DNA polymerase. The reactions were performed under the following cycling conditions: 1 cycle at 94° C. for 3 minutes; 38 cycles of 94° C. for 30 seconds, 60° C. for 30 seconds, 72° C. for 1.5 minutes; 1 cycle at 72° C. for 10 minutes.

The PCR products (20 µL) of the expected sizes representing the genomic sequence flanking the 5' and 3' ends of the insert were isolated by gel electrophoresis on a 2.0% agarose gel at 60 V for ~1 hour and visualized by ethidium bromide staining. The PCR fragments representing the 5' and 3' flanking sequences were excised from the gel and purified using the QIAquick Gel Extraction Kit (Qiagen, catalog # 28704) following the procedure supplied by the manufacturer. The purified PCR products were then sequenced with the initial PCR primers using dye-terminator chemistry.

The control reactions containing no template as well as the reactions containing non-transgenic corn DNA did not generate a PCR product with either primer set, as expected. PCR analysis of the corn rootworm event MON863 DNA generated the expected size products of 508 bp representing the 5' flanking sequence (SEQ ID NO:3) when using primers A and B having SEQ ID NOs: 9 and 10 and 584 bp representing the 3' flanking sequence (SEQ ID NO:4) when using primers D and C having SEQ ID NOs: 11 and 12.

Sequence data indicated that the 5' amplicon, i.e., SEQ ID NO:3, consisted of 266 bp of the 5' end of the 35S promoter at the 5' end of the insert followed by 242 bp of corn genomic flanking DNA. Sequence data indicated that the 3' amplicon, i.e., SEQ ID NO:4, consisted of 360 bp of the tahsp17 3' polyadenylation sequence which defines the 3' end of the insert, immediately followed by 224 bp of corn genomic flanking DNA.

Agronomically and commercially important products and/or compositions of matter including but not limited to animal feed, commodities, and corn products and by-products that are intended for use as food for human consumption or for use in compositions that are intended for human consumption including but not limited to corn flour, corn meal, corn syrup, corn oil, corn starch, popcorn, corn cakes, cereals containing corn and corn by-products, and the like are intended to be within the scope of the present invention if these products and compositions of matter contain detectable amounts of the nucleotide sequences set forth herein as being diagnostic for the corn event MON863.

Seed comprising the MON863 corn event have been deposited by the Applicant with American Type Culture Collection (ATCC), 10801 University Boulevard, Manassas, Va., USA ZIP 20110-2209 on Oct. 17, 2000. The ATCC provided the Applicant with a deposit receipt, assigning the ATCC Deposit Accession No. PTA-2605 to the corn *Zea mays* event MON863 PV-ZMIR13.

Those of skill in the art, in light of these examples, should appreciate that many changes can be made to the foregoing assays to detect DNA derived from corn event MON863 in a sample. For example, a primer set comprising one primer complementary to corn genome DNA and another primer complementary to sequences within the insert are envisioned. Furthermore, any of various hybridization assays described earlier using DNA probes complementary to the novel nucleic acid sequences located at transgene/genome junctions are envisioned as well.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

What is claimed is:

1. A biological sample derived from corn event MON863 plant, tissue, or seed, wherein said sample comprises a nucleotide sequence which is or is complementary to a sequence selected from the group consisting of SEQ ID NO:1 and SEQ ID NO:2, wherein said nucleotide sequence is detectable in said sample using a nucleic acid amplification or nucleic acid hybridization method and, wherein a representative sample of said corn event MON863 seed of has been deposited with American Type Culture Collection (ATCC) with Accession No. PTA-2605.

2. The biological sample of claim 1, wherein said biological sample comprises plant, tissue, or seed of transgenic corn event MON863.

3. The biological sample of claim 2, wherein said biological sample is a DNA sample extracted from the transgenic corn plant event MON863, and wherein said DNA sample comprises one or more of the nucleotide sequences selected from the group consisting of SEQ ID NO:1, SEQ ID NO:2, and the complement thereof.

4. The biological sample of claim 3, wherein said biological sample is selected from the group consisting of corn flour, corn meal, corn syrup, corn oil, corn starch, and cereals manufactured in whole or in part to contain corn by-products.

5. An extract derived from corn event MON863 plant, tissue, or seed and comprising a nucleotide sequence which is or is complementary to a sequence selected from the group consisting of SEQ ID NO: 1 and SEQ ID NO:2, wherein a representative sample of said corn event MON863 seed of has been deposited with American Type Culture Collection (ATCC) with Accession No. PTA-2605.

6. The extract of claim 5, wherein said nucleotide sequence is detectable in said extract using a nucleic acid amplification or nucleic acid hybridization method.

7. The extract of claim 6, wherein said extract comprises plant, tissue, or seed of transgenic corn plant event MON863.

8. The extract of claim 7, further comprising a composition selected from the group consisting of corn flour, corn meal, corn syrup, corn oil, corn starch, and cereals manufactured in whole or in part to contain corn by-products, wherein said composition comprises a detectable amount of said nucleotide sequence.

9. A corn event MON863, wherein a representative sample of seed of said corn event has been deposited with American Type Culture Collection (ATCC) with Accession No. PTA-2605.

10. Plant parts of the corn event of claim 9.

11. Seed comprising corn event MON863, wherein said seed comprises a DNA molecule selected from the group consisting of SEQ ID NO: 1 and SEQ ID NO:2, and wherein a representative sample of corn event MON863 seed of has been deposited with American Type Culture Collection (ATCC) with Accession No. PTA-2605.

* * * * *

```
                            SEQUENCE LISTING

<160> NUMBER OF SEQ ID NOS: 21

<210> SEQ ID NO 1
    <211> LENGTH: 20
    <212> TYPE: DNA
    <213> ORGANISM: Artificial Sequence
    <220> FEATURE:
    <223> OTHER INFORMATION: 5' junction sequence
    <220> FEATURE:
    <221> NAME/KEY: DNA
    <222> LOCATION: (1)..(20)
    <223> OTHER INFORMATION: 5' junction sequence

<400> SEQUENCE: 1
agcttggtac actttggggt                                                  20

<210> SEQ ID NO 2
    <211> LENGTH: 20
    <212> TYPE: DNA
    <213> ORGANISM: Artificial Sequence
    <220> FEATURE:
    <223> OTHER INFORMATION: 3' junction sequence
    <220> FEATURE:
    <221> NAME/KEY: DNA
    <222> LOCATION: (1)..(20)
    <223> OTHER INFORMATION: 3' junction sequence

<400> SEQUENCE: 2
ggaattcggt ctccctatag                                                  20

<210> SEQ ID NO 3
    <211> LENGTH: 508
    <212> TYPE: DNA
    <213> ORGANISM: Artificial Sequence
    <220> FEATURE:
    <223> OTHER INFORMATION: 5' genome + insert sequence
    <220> FEATURE:
    <221> NAME/KEY: DNA
    <222> LOCATION: (1)..(508)
    <223> OTHER INFORMATION: 5' genome + insert sequence
```

<400> SEQUENCE: 3

```
gtcttgcgaa ggatagtggg attgtgcgtc atcccttacg tcagtggaag tatcacatca      60
atccacttgc tttgaagacg tggttggaac gtcttctttt tccacgatgc tcctcgtggg     120
tgggggtcca tctttgggac cactgtcggc agaggcatct tgaatgatag cctttccttt     180
atcgcaatga tggcatttgt aggtgccacc ttccttttct actgtccttt tgatgaagtg     240
acaggtagga tcggaaagct tggtacactt tggggtgaac acccatccga acaagtaggg     300
tcaatagttc agcatttagg ccgtaacatt tagcaaaaaa ctaatcttaa acccaacaag     360
tgctctccga accaagctag atagtctcct atcactaggc tcaccaacca acctggactt     420
tgattctttc ttattattct aaccgggata taaaaaccat aaggattgtt ccagccaag     480
agttcccata tgacataagc gctcttgg                                         508
```

<210> SEQ ID NO 4
<211> LENGTH: 584
<212> TYPE: DNA
<213> ORGANISM: Artificial Sequence
<220> FEATURE:
<223> OTHER INFORMATION: 3' insert + genome sequence
<220> FEATURE:
<221> NAME/KEY: DNA
<222> LOCATION: (1)..(584)
<223> OTHER INFORMATION: 3' insert + genome sequence

<400> SEQUENCE: 4

```
ctgatcattg gtgctgagtc cttcgtctcc aacgagaaga tctacatcga caagatcgag      60
ttcatccccg tccagctgtg ataggaactc tgattgaatt ctgcatgcgt ttggacgtat     120
gctcattcag gttggagcca atttggttga tgtgtgtgcg agttcttgcg agtctgatga     180
gacatctctg tattgtgttt cttttcccag tgttttctgt acttgtgtaa tcggctaatc     240
gccaacagat tcggcgatga ataaatgaga aataaattgt tctgattttg agtgcaaaaa     300
aaaaggaatt agatctgtgt gtgttttttg gatccccggg gcggccgcgg ggaattcggt     360
ctccctatag agcagagcat agtgacaaaa gttccattta gatatggttg tatcatatgt     420
atataaagaa tgtactcgca atgaactggc taagtccaac caaccatgat ggcagcctgc     480
cccctatag ccaaagcaag cgatagcaaa tagtgatttt atggagtaag cttcgctccg     540
cgccaattag aaaaaagtga aaagactcta tgctctgctc atat                       584
```

<210> SEQ ID NO 5
<211> LENGTH: 242
<212> TYPE: DNA
<213> ORGANISM: corn
<220> FEATURE:
<221> NAME/KEY: DNA
<222> LOCATION: (1)..(242)
<223> OTHER INFORMATION: 5' corn genome sequence

<400> SEQUENCE: 5

```
actttggggt gaacacccat ccgaacaagt agggtcaata gttcagcatt taggccgtaa      60
catttagcaa aaaactaatc ttaaacccaa caagtgctct ccgaaccaag ctagatagtc     120
tcctatcact aggctcacca accaacctgg actttgattc tttcttatta ttctaaccgg     180
gatataaaaa ccataaggat tgtttccagc caagagttcc catatgacat aagcgctctt     240
gg                                                                      242
```

```
<210> SEQ ID NO 6
<211> LENGTH: 224
<212> TYPE: DNA
<213> ORGANISM: corn
<220> FEATURE:
<221> NAME/KEY: DNA
<222> LOCATION: (1)..(224)
<223> OTHER INFORMATION: 3' corn genome sequence

<400> SEQUENCE: 6
ctccctatag agcagagcat agtgacaaaa gttccattta gatatggttg tatcatatgt      60
atataaagaa tgtactcgca atgaactggc taagtccaac caaccatgat ggcagcctgc     120 cccctatag ccaaagcaag cgatagcaaa tagtgatttt atggagtaag cttcgctccg     180
cgccaattag aaaaaagtga aaagactcta tgctctgctc atat                     224

<210> SEQ ID NO 7
<211> LENGTH: 266
<212> TYPE: DNA
<213> ORGANISM: Artificial Sequence
<220> FEATURE:
<223> OTHER INFORMATION: 5' insert sequence
<220> FEATURE:
<221> NAME/KEY: DNA
<222> LOCATION: (1)..(266)
<223> OTHER INFORMATION: 5' insert sequence

<400> SEQUENCE: 7
gtcttgcgaa ggatagtggg attgtgcgtc atcccttacg tcagtggaag tatcacatca      60
atccacttgc tttgaagacg tggttggaac gtcttctttt tccacgatgc tcctcgtggg     120
tgggggtcca tctttgggac cactgtcggc agaggcatct tgaatgatag cctttccttt     180
atcgcaatga tggcatttgt aggtgccacc ttccttttct actgtccttt tgatgaagtg     240
acaggtagga tcggaaagct tggtac                                         266

<210> SEQ ID NO 8
<211> LENGTH: 360
<212> TYPE: DNA
<213> ORGANISM: Artificial Sequence
<220> FEATURE:
<223> OTHER INFORMATION: 3' insert sequence
<220> FEATURE:
<221> NAME/KEY: DNA
<222> LOCATION: (1)..(360)
<223> OTHER INFORMATION: 3' insert sequence

<400> SEQUENCE: 8
ctgatcattg gtgctgagtc cttcgtctcc aacgagaaga tctacatcga caagatcgag      60
ttcatccccg tccagctgtg ataggaactc tgattgaatt ctgcatgcgt ttggacgtat     120
gctcattcag gttggagcca atttggttga tgtgtgtgcg agttcttgcg agtctgatga     180
gacatctctg tattgtgttt cttccccag tgttttctgt acttgtgtaa tcggctaatc     240
gccaacagat tcggcgatga ataaatgaga aataaattgt tctgattttg agtgcaaaaa     300
aaaaggaatt agatctgtgt gtgttttttg gatccccggg gcggccgcgg ggaattcggt     360

<210> SEQ ID NO 9
<211> LENGTH: 22
<212> TYPE: DNA
<213> ORGANISM: Artificial Sequence
<220> FEATURE:
<223> OTHER INFORMATION: 5' 5' primer
```

```
<220> FEATURE:
<221> NAME/KEY: DNA
<222> LOCATION: (1)..(22)
<223> OTHER INFORMATION: 5' flanking sequence 5' primer

<400> SEQUENCE: 9
gtcttgcgaa ggatagtggg at                                              22

<210> SEQ ID NO 10
<211> LENGTH: 22
<212> TYPE: DNA
<213> ORGANISM: Artificial Sequence
<220> FEATURE:
<223> OTHER INFORMATION: 5' 3' primer
<220> FEATURE:
<221> NAME/KEY: DNA
<222> LOCATION: (1)..(22)
<223> OTHER INFORMATION: 5' flanking sequence 3' primer

<400> SEQUENCE: 10
catatgacat aagcgctctt gg                                              22

<210> SEQ ID NO 11
<211> LENGTH: 23
<212> TYPE: DNA
<213> ORGANISM: Artificial Sequence
<220> FEATURE:
<223> OTHER INFORMATION: 3' 5' primer
<220> FEATURE:
<221> NAME/KEY: DNA
<222> LOCATION: (1)..(23)
<223> OTHER INFORMATION: 3' flanking sequence 5' primer

<400> SEQUENCE: 11
ctgatcattg gtgctgagtc ctt                                             23

<210> SEQ ID NO 12
<211> LENGTH: 22
<212> TYPE: DNA
<213> ORGANISM: Artificial Sequence
<220> FEATURE:
<223> OTHER INFORMATION: 3' 3' primer
<220> FEATURE:
<221> NAME/KEY: DNA
<222> LOCATION: (1)..(22)
<223> OTHER INFORMATION: 3' flanking sequence 3' primer

<400> SEQUENCE: 12
agactctatg ctctgctcat at                                              22

<210> SEQ ID NO 13
<211> LENGTH: 27
<212> TYPE: DNA
<213> ORGANISM: Artificial Sequence
<220> FEATURE:
<223> OTHER INFORMATION: 5' genome walker primer 1
<220> FEATURE:
<221> NAME/KEY: DNA
<222> LOCATION: (1)..(27)
<223> OTHER INFORMATION: 5' genome walker primer 1

<400> SEQUENCE: 13
gaacgtcttc tttttccacg atgctcc                                         27

<210> SEQ ID NO 14
<211> LENGTH: 26
<212> TYPE: DNA
<213> ORGANISM: Artificial Sequence
```

```
<220> FEATURE:
<223> OTHER INFORMATION: 5' genome walker primer 2
<220> FEATURE:
<221> NAME/KEY: DNA
<222> LOCATION: (1)..(26)
<223> OTHER INFORMATION: 5' genome walker primer 2

<400> SEQUENCE: 14
tcggcagagg catcttgaat gatagc                                               26

<210> SEQ ID NO 15
<211> LENGTH: 26
<212> TYPE: DNA
<213> ORGANISM: Artificial Sequence
<220> FEATURE:
<223> OTHER INFORMATION: 3' genome walker primer 1
<220> FEATURE:
<221> NAME/KEY: DNA
<222> LOCATION: (1)..(26)
<223> OTHER INFORMATION: 3' genome walker primer 1

<400> SEQUENCE: 15
gcgagtctga tgagacatct ctgtat                                               26

<210> SEQ ID NO 16
<211> LENGTH: 27
<212> TYPE: DNA
<213> ORGANISM: Artificial Sequence
<220> FEATURE:
<223> OTHER INFORMATION: 3' genome walker primer 2
<220> FEATURE:
<221> NAME/KEY: DNA
<222> LOCATION: (1)..(27)
<223> OTHER INFORMATION: 3' genome walker primer 2

<400> SEQUENCE: 16
aatttggttg atgtgtgtgc gagttct                                              27

<210> SEQ ID NO 17
<211> LENGTH: 416
<212> TYPE: DNA
<213> ORGANISM: Cauliflower mosaic virus
<220> FEATURE:
<221> NAME/KEY: DNA
<222> LOCATION: (1)..(416)
<223> OTHER INFORMATION: CaMV35S AS4 promoter sequence

<400> SEQUENCE: 17
ttctagagga tcagcatggc gcccaccgtg atgatggcct cgtcggccac cgccgtcgct          60
ccgttcctgg ggctcaagtc caccgccagc ctccccgtcg cccgccgctc ctccagaagc         120
ctcggcaacg tcagcaacgg cggaaggatc cggtgcatgc aggtaacaaa tgcatcctag         180
ctagtagttc tttgcattgc agcagctgca gctagcgagt tagtaatagg aagggaactg         240
atgatccatg catggactga tgtgtgttgc ccatcccatc ccatcccatt tcccaaacga         300
accgaaaaca ccgtactacg tgcaggtgtg gccctacggc aacaagaagt cgagacgct          360 gtcgtacctg ccgccgctgt cgaccggcgg gcgcatccgc tgcatgcagg ccatgg            416

<210> SEQ ID NO 18
<211> LENGTH: 75
<212> TYPE: DNA
<213> ORGANISM: Triticum aestivum
<220> FEATURE:
<221> NAME/KEY: DNA
<222> LOCATION: (1)..(75)
<223> OTHER INFORMATION: L-Ta.hcb1 untranslated leader sequence
```

-continued

```
<400> SEQUENCE: 18
ctagaaccat cttccacaca ctcaagccac actattggag aacacacagg gacaacacac 60
cataagatcc aaggg 75

<210> SEQ ID NO 19
<211> LENGTH: 804
<212> TYPE: DNA
<213> ORGANISM: Oryza sp.
<220> FEATURE:
<221> NAME/KEY: DNA
<222> LOCATION: (1)..(804)
<223> OTHER INFORMATION: I-OS.Act1 rice actin intron sequence
<400> SEQUENCE: 19
accgtcttcg gtacgcgctc actccgccct ctgcctttgt tactgccacg tttctctgaa 60
tgctctcttg tgtggtgatt gctgagagtg gtttagctgg atctagaatt acactctgaa 120
atcgtgttct gcctgtgctg attacttgcc gtcctttgta gcagcaaaat atagggacat 180
ggtagtacga aacgaagata gaacctacac agcaatacga gaaatgtgta atttggtgct 240
tagcggtatt tatttaagca catgttggtg ttatagggca cttggattca gaagtttgct 300
gttaatttag gcacaggctt catactacat gggtcaatag tatagggatt catattatag 360
gcgatactat aataatttgt tcgtctgcag agcttattat ttgccaaaat tagatattcc 420
tattctgttt ttgtttgtgt gctgttaaat tgttaacgcc tgaaggaata aatataaatg 480
acgaaatttt gatgtttatc tctgctcctt tattgtgacc ataagtcaag atcagatgca 540
cttgttttaa atattgttgt ctgaagaaat aagtactgac agtattttga tgcattgatc 600
tgcttgtttg ttgtaacaaa atttaaaaat aaagagtttc ctttttgttg ctctccttac 660
ctcctgatgg tatctagtat ctaccaactg acactatatt gcttctcttt acatacgtat 720
cttgctcgat gccttctccc tagtgttgac cagtgttact cacatagtct ttgctcattt 780
cattgtaatg cagataccaa gcgg 804

<210> SEQ ID NO 20
<211> LENGTH: 1984
<212> TYPE: DNA
<213> ORGANISM: Artificial Sequence
<220> FEATURE:
<223> OTHER INFORMATION: non-native Cry3Bb variant 11231mv1
<220> FEATURE:
<221> NAME/KEY: DNA
<222> LOCATION: (1)..(1984)
<223> OTHER INFORMATION: non-native Cry3Bb variant
<400> SEQUENCE: 20
ccatggccaa ccccaacaat cgctccgagc acgacacgat caaggtcacc cccaactccg 60
agctccagac caaccacaac cagtacccgc tggccgacaa ccccaactcc accctggaag 120
agctgaacta caaggagttc ctgcgcatga ccgaggactc ctccacggag gtcctggaca 180
actccaccgt caaggacgcc gtcgggaccg gcatctccgt cgttgggcag atcctgggcg 240
tcgttggcgt ccccttcgca ggtgctctca cctccttcta ccagtccttc ctgaacacca 300
tctggccctc cgacgccgac ccctggaagg ccttcatggc ccaagtcgaa gtcctgatcg 360
acaagaagat cgaggagtac gccaagtcca aggccctggc cgagctgcaa ggcctgcaaa 420
acaacttcga ggactacgtc aacgcgctga actcctggaa gaagacgcct ctgtccctgc 480
gctccaagcg ctcccagggc cgcatccgcg agctgttctc ccaggccgag tcccacttcc 540
gcaactccat gccgtccttc gccgtctcca agttcgaggt cctgttcctg cccacctacg 600
```

-continued

```
cccaggctgc caacacccac ctcctgttgc tgaaggacgc ccaggtcttc ggcgaggaat    660
ggggctactc ctcggaggac gtcgccgagt tctaccgtcg ccagctgaag ctgacccaac    720
agtacaccga ccactgcgtc aactggtaca acgtcggcct gaacggcctg aggggctcca    780
cctacgacgc atgggtcaag ttcaaccgct tccgcaggga gatgaccctg accgtcctgg    840
acctgatcgt cctgttcccc ttctacgaca tccgcctgta ctccaagggc gtcaagaccg    900
agctgacccg cgacatcttc acggacccca tcttcctgct cacgaccctc cagaagtacg    960
gtcccacctt cctgtccatc gagaactcca tccgcaagcc ccacctgttc gactacctcc   1020
agggcatcga gttccacacg cgcctgaggc caggctactt cggcaaggac tccttcaact   1080
actggtccgg caactacgtc gagaccaggc cctccatcgg ctcctcgaag acgatcacct   1140
ccccttttcta cggcgacaag tccaccgagc ccgtccagaa gctgtccttc gacggccaga   1200
aggtctaccg caccatcgcc aacaccgacg tcgcggcttg gccgaacggc aaggtctacc   1260
tgggcgtcac gaaggtcgac ttctcccagt acgatgacca gaagaatgaa acctccaccc   1320
agacctacga ctccaagcgc aacaatggcc acgtctccgc ccaggactcc atcgaccagc   1380
tgccgcctga ccactgac gagccctgg agaaggccta ctcccaccag ctgaactacg   1440
cggagtgctt cctgatgcaa gaccgcaggg gcaccatccc cttcttcacc tggacccacc   1500
gctccgtcga cttcttcaac accatcgacg ccgagaagat cacccagctg cccgtggtca   1560
aggcctacgc cctgtcctcg ggtgcctcca tcattgaggg tccaggcttc accggtggca   1620
acctgctgtt cctgaaggag tcctcgaact ccatcgccaa gttcaaggtc accctgaact   1680
ccgctgcctt gctgcaacgc taccgcgtcc gcatccgcta cgcctccacc acgaacctgc   1740
gcctgttcgt ccagaactcc aacaatgact tcctggtcat ctacatcaac aagaccatga   1800
acaaggacga tgacctgacc taccagacct tcgacctcgc caccacgaac tccaacatgg   1860
gcttctcggg cgacaagaat gaactgatca ttggtgctga gtccttcgtc tccaatgaaa   1920
agatctacat cgacaagatc gagttcatcc ccgtccagct gtgataggaa ctctgattga   1980
attc                                                                1984
```

```
<210> SEQ ID NO 21
<211> LENGTH: 234
<212> TYPE: DNA
<213> ORGANISM: Triticum aestivum
<220> FEATURE:
<221> NAME/KEY: DNA
<222> LOCATION: (1)..(234)
<223> OTHER INFORMATION: T-Ta.Hsp17 termination and polyadenylation
      sequence

<400> SEQUENCE: 21
aattctgcat gcgtttggac gtatgctcat tcaggttgga gccaatttgg ttgatgtgtg     60
tgcgagttct tgcgagtctg atgagacatc tctgtattgt gtttcttttcc ccagtgtttt    120
ctgtacttgt gtaatcggct aatcgccaac agattcggcg atgaataaat gagaaataaa    180
ttgttctgat tttgagtgca aaaaaaagg aattagatct gtgtgtgttt tttg            234
```